United States Patent [19]

Gillis et al.

[11] 4,239,731

[45] Dec. 16, 1980

[54] APPARATUS FOR BIOCIDAL STERILIZATION USING CYCLIC SUBATMOSPHERIC PRESSURE CONDITIONING

[75] Inventors: John R. Gillis, Harborcreek; Frank E. Halleck, Erie, both of Pa.

[73] Assignee: American Sterilizer Company, Erie, Pa.

[21] Appl. No.: 96,489

[22] Filed: Nov. 21, 1979

Related U.S. Application Data

[62] Division of Ser. No. 850,846, Nov. 11, 1977, Pat. No. 4,203,943.

[51] Int. Cl.³ .................. A61L 5/00; A61L 1/00; A61L 3/00
[52] U.S. Cl. .................................. 422/112; 422/27; 422/33; 422/34; 422/114; 422/116
[58] Field of Search .................. 422/112, 114, 116, 27, 422/33, 34

[56] References Cited

U.S. PATENT DOCUMENTS

| | | | |
|---|---|---|---|
| 2,080,179 | 5/1937 | Memam et al. | 422/27 |
| 2,131,134 | 9/1938 | Baer et al. | 422/33 X |
| 2,188,371 | 1/1940 | Memam | 131/133 |
| 3,035,806 | 5/1962 | Hickey | 422/34 X |
| 3,206,275 | 9/1965 | Sair et al. | 422/34 X |
| 3,409,389 | 11/1968 | Bjork | 422/26 |
| 3,436,170 | 4/1969 | Lodge | 422/26 |
| 3,494,725 | 2/1970 | Irons et al. | 422/26 |
| 3,598,516 | 8/1971 | Shull et al. | 422/27 |
| 3,795,483 | 3/1974 | Crafingholt | 422/26 X |
| 3,861,875 | 1/1975 | Joslyn | 422/62 |
| 3,910,761 | 10/1975 | Hopkins | 422/108 |
| 3,954,406 | 5/1976 | Chamberlain | 422/34 X |

FOREIGN PATENT DOCUMENTS

| | | | |
|---|---|---|---|
| 3137 | of 1903 | United Kingdom | 422/27 |
| 488638 | 7/1938 | United Kingdom | 422/27 |
| 542554 | 1/1942 | United Kingdom | 422/27 |

OTHER PUBLICATIONS

S. S. Block—"Disinfection, Sterilization and Preservation", Publ. by Lee & Febiger, Phila., Pa. 1977, pp. 493–508.

J. J. Perkins, "Principles & Methods of Sterilization in Health Sciences", publ. by C. C. Thomas, Springville Ill, pp. 110–114, 150–152 & 501–530.

"Development in Industrial Microbiology", vol. 18, Society For Industrial Microbiology, pp. 335–351.

*Primary Examiner*—Barry Richman
*Attorney, Agent, or Firm*—Shanley, O'Neil and Baker

[57] ABSTRACT

Conditioning of goods for subsequent sterilization with a biocidal agent in a sealable chamber includes removal of air, and moistening and heating the goods to the desired temperature levels. Controlled evacuation of the chamber and coordinated admission of conditioning vapor into the chamber provides cyclic variations in chamber pressure between preselected subatmospheric pressures to subject goods in the chamber to a plurality of cyclic subatmospheric pressure pulses. The time required for the cyclic pressure variations is responsive to load characteristics, including heat and moisture absorption characteristics of the goods being conditioned, and is independent of prescribed times or direct measurement of load temperature. The subatmospheric pressure levels are selected based on the temperature-pressure relationship of the conditioning vapor so that chamber temperature during cyclic pulsing does not exceed the desired sterilization temperature.

9 Claims, 8 Drawing Figures

APPARATUS FOR BIOCIDAL STERILIZATION USING CYCLIC SUBATMOSPHERIC PRESSURE CONDITIONING

This is a division of application Ser. No. 850,846, filed Nov. 11, 1977, now U.S. Pat. No. 4,203,943 issued May 20, 1980, the entire disclosure of which is incorporated herein by reference.

This invention is concerned with sterilization of goods with chemically biocidal agents. In its more specific aspects, the invention is concerned with methods and apparatus for more effective and more accurate preparation of goods for biocidal gas sterilization and automated control of such conditioning of goods for biocidal gas sterilization.

Sterilization with a biocidal agent, e.g., with ethylene oxide gas, is utilized for sterilizing goods which could be damaged by the high temperature requirements of steam sterilization. Background on prior types of gas sterilizing processes and apparatus, and advantages of utilizing ethylene oxide, are covered in "Principles and Methods of Sterilization" by John J. Perkins, First Edition 1956, pages 325–334; Second Edition 1969, pages 501–530.

The effects of time, temperature, gas concentration and humidity are integrated in accomplishing the desired kill of microbial spores, vegetative bacteria and other microorganisms. Humidification and heating of the goods to be sterilized, and penetration of the sterilizing or biocidal gas, can be more effectively carried out if air is first evacuated from the sterilizing chamber and from any packaged goods, fabric-type goods, or goods with interstitial spaces to be sterilized. Therefore, the conditioning of goods for gas sterilization involving evacuation of the chamber is generally carried out prior to injection of a biocidal gas in order to avoid loss of such gas through evacuation.

Such conditioning can be carried out by first evacuating the chamber, then adding moisture to the chamber after evacuation is completed, and then adding the sterilizing gas at a desired higher pressure. It has been generally recognized that more complete removal of air and more rapid heat-up times are available with a cycle in which steam flows into and through the chamber while evacuating continues; see e.g., U.S. Pat. No. 3,598,516, dated Aug. 10, 1971.

In such steam flow conditioning practice, a timer sets a prescribed period for steam flow while evacuating of the chamber continues during conditioning of the goods. This prescribed time period is built into the control apparatus to provide for heating the most-difficult-to-heat load which might be encountered plus, usually, an added safety factor. This practice can extend the conditioning period much longer than necessary for most loads. A suggested alternative has been the packing of load sensors directly in the load to measure load temperature directly. But such a procedure places further burden on the operator and requires greater reliance on operator control.

The present invention requires neither prescribed times nor sensors placed in the load, but rather utilizes subatmospheric pressure cyclic pulsing and load-responsive characteristics of the goods to provide accurate and proficient conditioning for biocidal gas sterilization. The invention utilizes a controlled pulsing action for a condensable conditioning vapor, such as steam. This pulsing action provides a drive power for the conditioning vapor which further reduces cycle time.

The advantages of rapid heating and short conditioning times are made available while adding accuracy of conditioning and dependability of operation.

Other advantages and contributions of the invention will be more apparent from a more specific presentation of the methods and description of the apparatus shown in the accompanying drawings.

During load conditioning in accordance with the invention, the chamber is operated between preselected subatmospheric pressure levels to provide cyclic pulsing utilizing a condensable vapor having transferrable latent heat and moisture for conditioning the goods to be sterilized. Evacuation of the chamber and introduction of such vapor are controlled to provide cyclic variation in chamber pressure between such preselected subatmospheric pressure levels. The cyclic variation is independent of prescribed times in that the time duration of a pressure rise from lower to higher preselected subatmospheric pressure levels during a cyclic variation is responsive to characteristics of the goods being conditioned and can vary for differing loads. Such load characteristics include moisture and heat absorption properties of materials forming the load; load characteristics can also vary depending on the size and manner of packing the load.

As is known, chamber temperature is directly related to chamber pressure for a particular vapor, e.g., steam. Therefore, pressure levels are selected so as not to cause the temperature to exceed a desired final sterilization temperature for the goods to be sterilized. Cyclic variation of chamber pressure is carried out so as to provide a plurality of cyclic pulses. Since individual pulses are load responsive and independent of fixed time intervals, the total time duration of the load conditioning phase is independent of any prescribed time interval.

Load conditioning can be initiated by purging air from the sterilizing chamber by evacuating the chamber while simultaneously introducing the conditioning vapor into the chamber at a controlled rate to prevent overheating the load prior to cyclic pulsing. Conditioning can be further automated by establishing a time relation between corresponding phases of successive pulses. For example, the number of cyclic pulses can be automatically selected based on the time duration of pressure rise from the lower to the higher of the preselected subatmospheric pressure levels of consecutive cyclic pulses. In one embodiment, cyclic pulsing is terminated when the time duration of the pressure rise of two such consecutive pulses is approximately equal.

Figure 2:
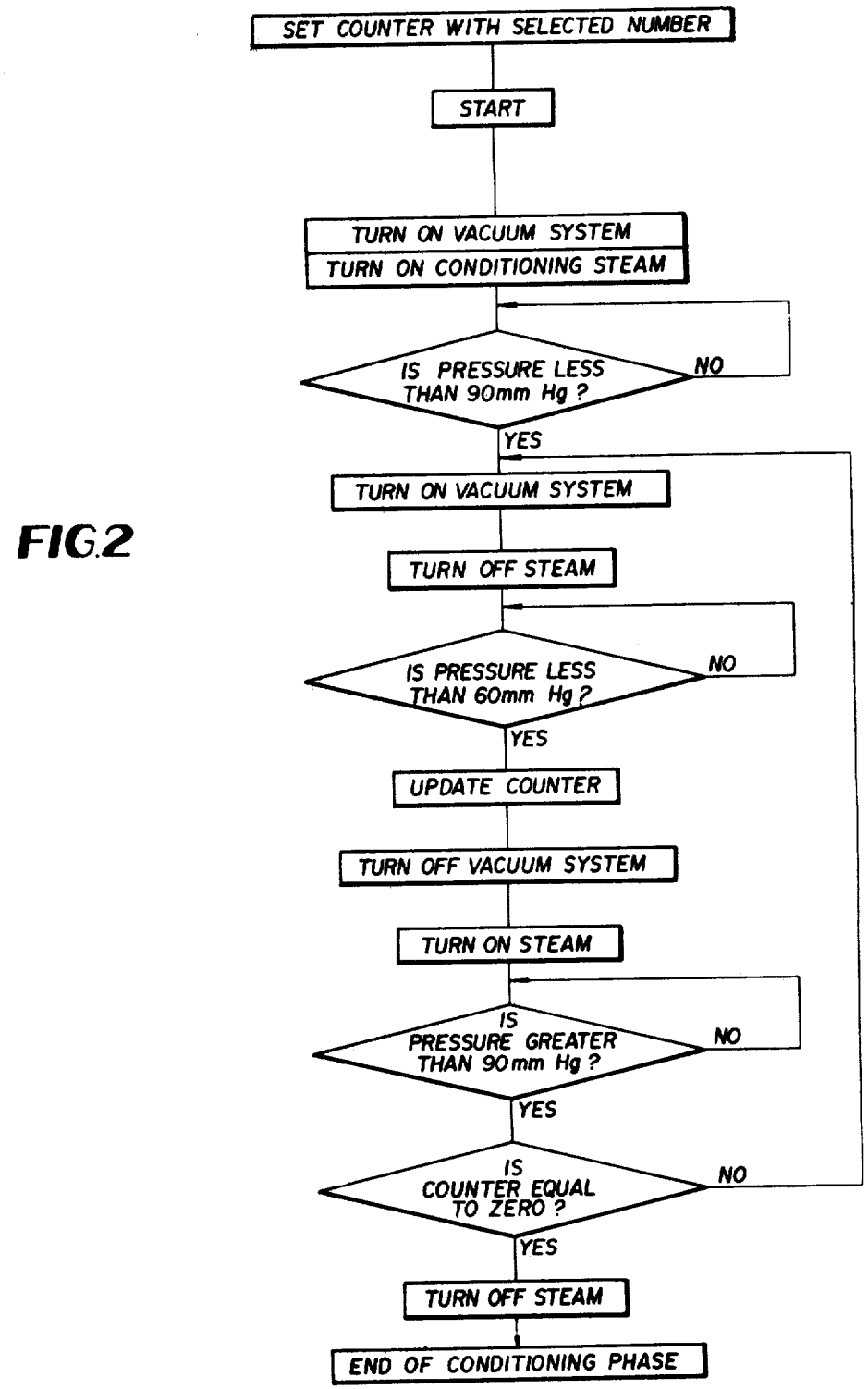
FIG. 2 is a process flow chart for carrying out a conditioning cycle in accordance with an embodiment of the invention in which material to be sterilized is subjected to a fixed number of conditioning pressure pulses.

Operation involving a fixed number of pulses is carried out in accordance with the process outlined in the flow chart of FIG. 2. The conditioning cycle includes the steps of subjecting the material to a fixed number of cyclic variations at subatmospheric pressures by alternately evacuating the conditioning chamber and increasing the pressure by admitting steam into the chamber at a controlled rate. An up-down counter, which counts the pulses, is pre-set, either manually or automatically, for the required number of pulses before commencing the cycle.

Operation can be initiated by a manual switch. The control logic provided by a master controller starts the chamber evacuation means and opens a power-operated exhaust valve to permit evacuation of the chamber. Steam is admitted into the chamber by actuation of a power-operated steam supply valve. The rate of flow of steam into and evacuation of the chamber can be coordinated so that the pressure in the chamber is reduced by the pump while steam is being admitted. The vacuum pump continues operation with steam flowing at a controlled rate into the chamber until the pressure within the chamber reaches a first predetermined subatmospheric level. The pressure within the chamber is continuously monitored by a pressure-sensing assembly mounted within the chamber.

When the pressure reaches an upper predetermined level, for example 90 mm Hg. abs., a first set of contacts in the pressure sensor is actuated to signal the controller to stop the flow of steam into the chamber. With the steam supply valve closed, the vacuum pump continues to operate to further reduce the pressure in the chamber, with pressure being monitored by the pressure sensing assembly. When the pressure reaches a lower predetermined level, for example, 60 mm Hg. abs., a second set of contacts in the pressure sensing assembly is actuated, signalling the controller to simultaneously close the exhaust valve and open the steam supply valve to admit a controlled flow of steam into the chamber.

Figure 4:
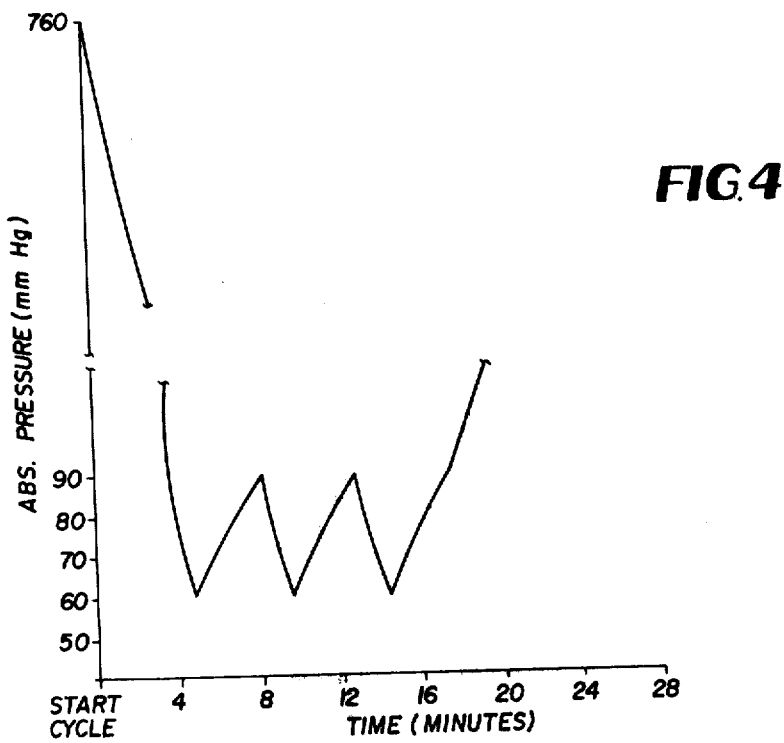
FIG. 4 is a graphic representation of chamber pressure versus time through the conditioning phase of FIG. 2.

In the latter condition, steam entering the chamber at a controlled rate will gradually increase the pressure, and consequently the temperature, in the chamber. This increase in pressure is continuously monitored by the pressure sensing assembly which, acting through the controller, maintains the apparatus in the stated mode until the pressure returns to or exceeds the upper predetermined pressure level. At this point, a third set of contacts in the pressure sensing assembly is actuated to simultaneously open the exhaust valve and close the steam supply valve. Again, this mode of operation is maintained constant, under the monitoring of the pressure sensing assembly, until the pressure within the chamber again reaches the lower predetermined level. At that time, the second set of contacts are again actuated to again close the exhaust valve and open the steam supply valve to repeat the evacuation phase of the cycle. Pressure pulses between fixed pressure levels during a typical conditioning phase are shown in FIG. 4. Cyclic pressure pulses can take place between differing pressure levels during the conditioning phase, but the upper pressure level is generally held at or slightly below the pressure corresponding to the desired sterilization temperature.

Figure 1:
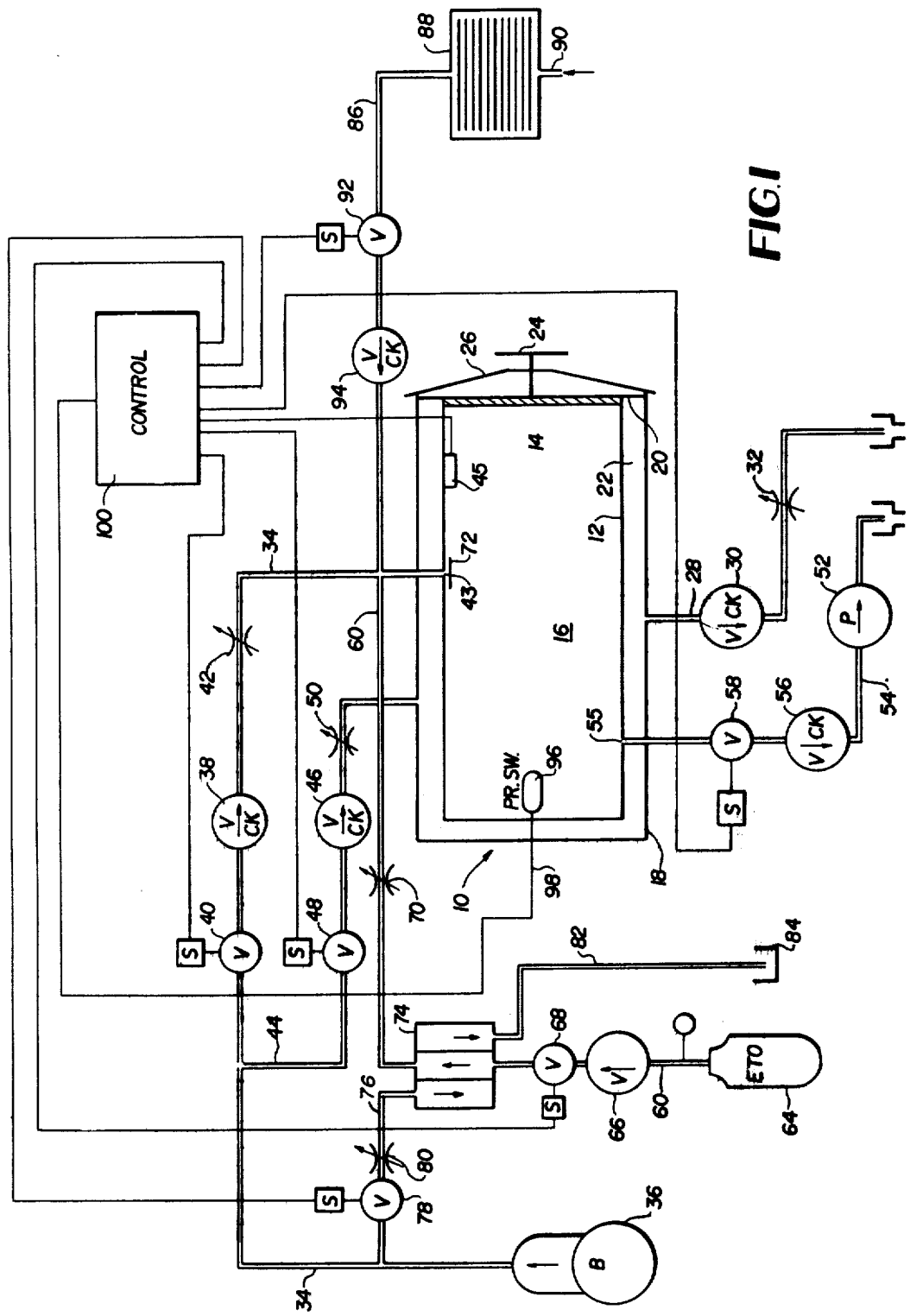
FIG. 1 is a schematic representation of apparatus in accordance with the invention.

Sterilizing apparatus embodying this invention is illustrated schematically in FIG. 1. Conventional sterilizing chamber configurations can be utilized. As shown, the apparatus includes a double-walled cylindrical structure indicated generally at 10 and having an inner, open-ended pressure vessel 12 defining, with an end closure, door 14, a sterilizing chamber 16. Pressure vessel 12 is supported within an outer wall 18 which is spaced outwardly from and circumscribes a major portion of vessel 12. An open end of the wall 18 is joined to the adjacent end of the inner pressure vessel 12 by an annular flange 20 to define a sealable space 22 between the inner and outer walls, commonly referred to as a jacket. Other heat insulating means for chamber 16 can be used.

The door 14 can be hinged or otherwise mounted at one side of the open end of the double wall structure to facilitate opening and closing the chamber 16. A conventional lock assembly can be used for door 14, e.g., a cam lock assembly, including an actuating lever or wheel 24 and locking cams 26, enabling the door to be firmly locked to tightly seal the chamber 16 during the sterilizing operation. A drain conduit 28 is fitted in a bottom portion of jacket wall 18, and a one-way check valve 30, connected in conduit 28, permits fluid to flow through conduit 28 to escape from the jacket 22. A variable-orifice flow-restrictor 32 is connected in the conduit 28 to enable the rate of flow through the conduit to be controlled so that the pressure, and thereby the temperature, within the jacket 22 can be regulated.

The sterilizer includes a plumbing system for supplying conditioning vapor and biocidal sterilizing gas to chamber 16, and steam to the jacket 22. The plumbing system is illustrated as including a main steam supply line or conduit 34 connected to a source of low-pressure steam, such as boiler 36, for supplying steam as a conditioning vapor, through one-way check valve 38, solenoid-actuated cut-off valve 40, and variable-orifice flow-restrictor 42, to an inlet 43 in sterilizing chamber 16. A branch conduit 44, connected in the main steam line 34 upstream of check valve 38, supplies steam to the jacket 22 to help insulate the inner pressure vessel 12 against heat loss. A temperature sensor, for example a thermocouple 45, is mounted on the wall of chamber 12 to continuously monitor the temperature of the wall which closely corresponds to the temperature of the steam in jacket 22. This measured temperature is employed to control actuation of solenoid-actuated valve 48 which, together with one-way check valve 46, and a variable-orifice flow-restrictor 50 in line 44 and check valve 30 and flow-restrictor 32 in drain line 28, control steam flow through conduit 44 to jacket 22.

The pressure within sterilizing chamber 16, and the flow of vapor or gases through that chamber during the conditioning phase of the cycle is controlled by a chamber exhaust system including suitable evacuating means such as a vacuum pump or ejector 52 connected, through exhaust line or conduit 54, to an outlet 55, which is shown in the bottom of sterilizing chamber 16 but which can be located at any convenient location. One-way check valve 56 and solenoid-actuated shut-off valve 58 are connected in exhaust line 54 to regulate the flow through the exhaust line. The temperature and pressure within the sterilizing chamber 16 may be regulated in part by this arrangement.

Sterilant supply means for supplying a controlled flow of biocidal gas, such as ethylene oxide, to the sterilizing chamber 16 includes a supply line or conduit 60 connected between conduit 34 downstream of check valve 38 and a source of the biocidal gas, indicated in FIG. 1 as a pressurized container or bottle 64. Flow through the conduit 60 is regulated by one-way check valve 66, solenoid-actuated shut-off valve 68, and a variable-orifice flow-restrictor 70. A baffle 72 mounted within the interior of chamber 16 adjacent the inlet 43 provides for a more uniform distribution of biocidal gas entering the chamber 16.

The temperature of the biocidal gas supplied to the chamber 16 can be regulated by a heat exchanger 74 connected in the line 60, in heat exchange relation with steam supplied through a conduit 76 connected in the main steam line 34. A solenoid-actuated shut-off valve 78 and a variable-orifice flow-restrictor 80, connected in line 76, regulate the flow of steam through the heat exchanger 74 and thereby the temperature of the biocidal gas flowing into chamber 16. Steam is exhausted from the heat exchanger 74 through a suitable conduit 82 to a sump or drain 84.

After sterilization, air flow through the chamber 16 is provided by air supply line 86 connected in the chamber supply line 34 downstream of the steam control valves 38, 40 and flow-restrictor 42. Air is supplied to the air line 86 through a suitable filter 88 having an inlet 90 open to the atmosphere. A solenoid-actuated shut-off valve 92 and one-way check valve 94 control flow through line 86. Since air flows through or into chamber 16 only when the pressure within the chamber is below atmosphere, atmospheric air pressure is sufficient to provide the necessary air flow. Filter 88 is of a type to effectively remove bacteria from the air and can also include other air sterilizing means.

In the embodiment of FIG. 1, a pressure sensing assembly 96 is mounted within chamber 16. Chamber pressure signals generated by the pressure sensing assembly 96 are supplied, through suitable electrical connections indicated by line 98, to a central control 100. Pressure sensing assembly 96 includes a first set of contacts which are actuated upon the pressure within the chamber 16 being initially lowered to the upper predetermined pressure to thereby generate a signal for the control 100 to actuate the solenoid of the inlet valve 40 to stop the flow of steam. Valve 40 can be a conventional, normally-closed, energized-open valve so that the control de-energizes the solenoid to close the valve. Power means other than a solenoid may be employed to control operation of the inlet and exhaust valves.

A second set of contacts in pressure sensing assembly 96 are actuated to generate a signal each time the pressure in chamber 16 reaches the lower predetermined level. This signal is utilized by the control 100 to operate the solenods of both the inlet valve 40 and the exhaust valve 58 to open the inlet valve and close the exhaust valve. This results in an increase in pressure within the chamber to the upper predetermined level. When approaching the upper pressure level in this manner, a third set of contacts in the pressure sensing assembly 96 is actuated, signalling control 100 to operate the solenoids to close inlet valve 40 and open exhaust valve 58 each time the upper predetermined pressure is reached from a lower pressure. The function of the first and third set of contacts may be achieved by a single set of contacts, but the control is simplified by using separate contacts which are actuated when the desired pressure is attained from higher and lower pressures. It is also possible to use separate contacts or other sensors to generate signals each time the lower pressure is reached, and these separate sensors may have different settings if desired to change the lower pressure of the individual pressure pulses.

Figure 3:
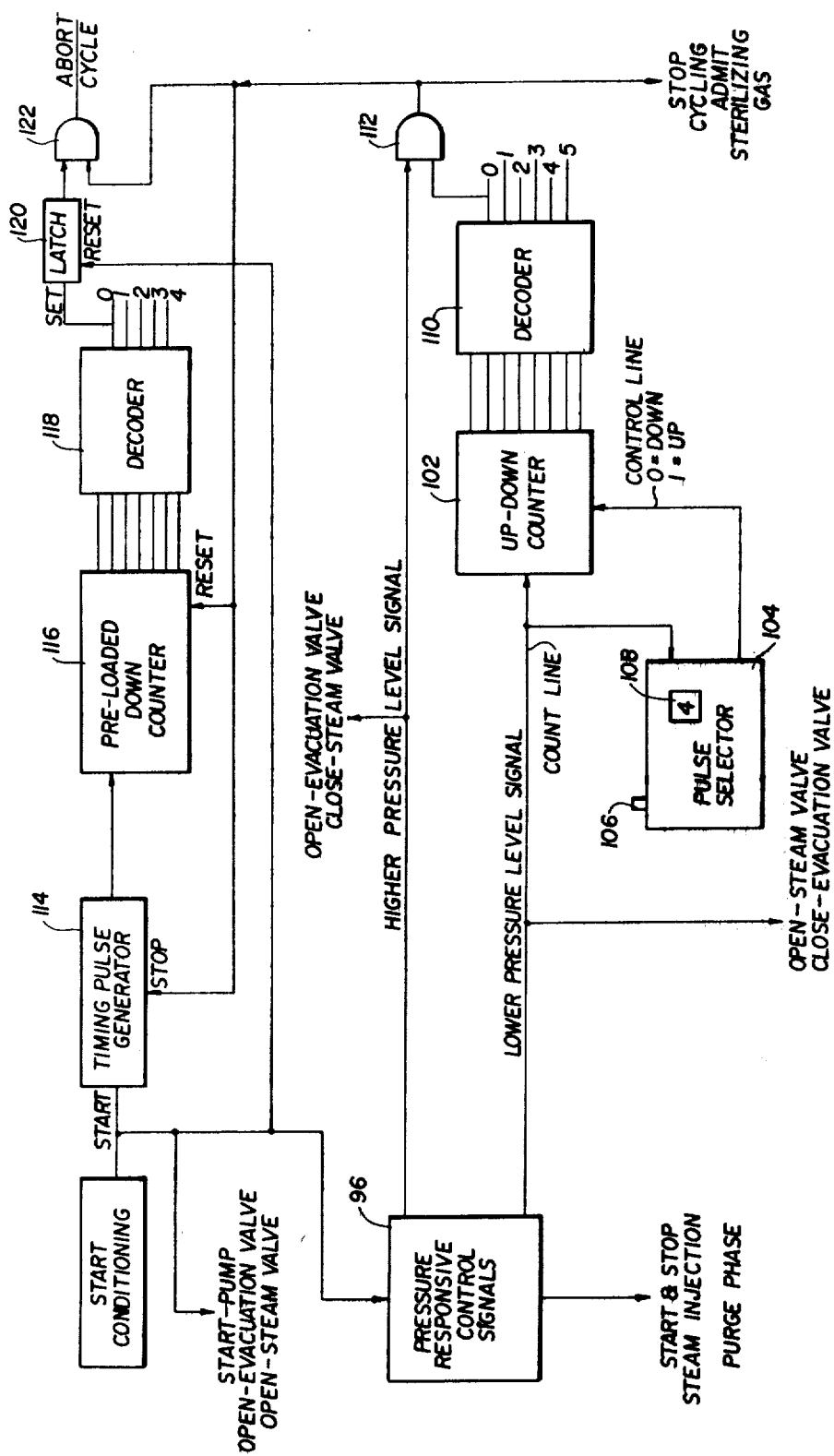
FIG. 3 is a schematic representation of control logic apparatus for carrying out conditioning in accordance with the process of FIG. 2.

Controller 100 includes a counter mechanism, preferably in the form of a solid state up-down counter illustrated schematically in FIG. 3, which counts the number of actuations of the contacts in pressure sensing assembly 96. After a predetermined number of cyclic pulses, when the pressure within chamber 16 reaches the upper predetermined subatmospheric level, actuation of the third set of contacts in pressure sensing assembly 96 results in the shut-off valve 40 being closed and shut-off valve 58 remaining closed. At the same time, shut-off valve 78 is opened to permit steam to flow through the heat exchanger 74 and shut-off valve 68 in biocidal gas supply line 60 is opened to permit biocidal gas to flow through the heat exchanger. Biocidal gas then flows through flow-restrictor 70 into chamber 16 to pressurize the chamber to the required level and the pressure is held for the required time to complete desired sterilization of the material in the chamber.

After completion of the biocidal gas treatment phase of the sterilization process, the interior of the chamber 16 can be flushed with filtered air by initially opening the valve 58 and operating the vacuum pump 52 to withdraw the residual biocidal gas from the chamber. The shut-off valve 58 is then closed and shut-off valve 92 opened to permit filtered air to enter the chamber. Shut-off valve 92 may then be closed and the air withdrawn by opening valve 58, and the process repeated as necessary to flush the biocidal gas from the articles being sterilized. Alternatively, the chamber can be flushed by simultaneously operating the evacuating pump and permitting air to flow into the chamber.

The final step in the sterilization process will normally consist of permitting filtered air at atmospheric pressure to enter the chamber and to stabilize the pressure throughout the sterilized articles whereupon the door 14 may be opened and the sterilized articles removed.

During the conditioning phase of the sterilizing process, air is withdrawn from porous articles to be processed and, in turn, the steam admitted to the chamber permeates the articles. The articles are heated from the latent heat of the steam which condenses on and within the articles, thereby simultaneously moistening and conditioning them for subsequent sterilization by the biocidal gas. As the outer layers of a load of material become heated, the steam penetrates deeper before it is condensed until eventually the load is completely permeated with steam and is heated and moistened substantially uniformly throughout. The pressure pulsing has been found to greatly facilitate steam penetration and air removal so that a more thorough and uniform conditioning is achieved.

With a controlled rate of admission of steam into the chamber during the repressurization phase of the cyclic pulses, the rate of condensation, and consequently the heating and humidification of the sterilizer load, will directly affect the length of time required for the chamber to become repressurized from the second, lower pressure level to the upper predetermined pressure level. It has been determined that, when the repressurization phase of two successive pulses requires substantially the same time, the load has been thoroughly conditioned, i.e., moistened and heated throughout. By measuring the time of the repressurization phases of each pulse, and comparing these times for successive pulses, the conditioning phase of the sterilization cycle can be terminated automatically when two succeeding measured times are substantially equal. This fully automated conditioning method is dependent directly upon the pressure which is continuously monitored in the chamber 16.

Experience has shown that conditioning can also be carried out with a fixed number of pulses. With normal steam flow it has been determined that four such cyclic pulses will adequately condition standard types of hospital loads including a devised pack considered to be the most difficult load to be encountered in the operation of a modern hospital. In operating a sterilizer according to the fixed number of pulses method, when four pulses have been completed, a counter automatically terminates the pulse conditioning phase in preparation for the sterilization phase. The total time duration for such four pulses will vary according to load characteristics.

FIG. 3 illustrates schematically the electronic control system for controlling the conditioning of material to be sterilized through a predetermined number of conditioning pulses, following the steps outlined in the flow diagram of FIG. 2. The control system includes a conventional up-down counter 102 which can be up-counted by feeding a signal in on the "count" line when the "control" line is in a given state and which can be down-counted by feeding a signal in on the "count" line when the "control" line is in a different given state. Before the process is begun, up-down counter 102 is loaded with a predetermined count which corresponds to the number of cyclic pulses which are to be used for the conditioning phase. This may be done automatically, that is with the number of pulses preset and fixed for a particular sterilizer; or, as shown in FIG. 3, can be set by depressing the button 106 on selector 104 the appropriate number of times. The pulse selector 104 is a conventional pulse generator, arranged so that the number of times that the button 106 is depressed appears on a display window 108.

The outputs of up-down counter 102 are connected to a decoder 104, each output line of which is representative of a given number. Thus, at the time that the initial number of pulses are loaded into counter 102, the corresponding output line of decoder 110 has a signal thereon. When this initial number of pulses is counted down to zero, then the zero output line of decoder 110 has a signal thereon. This indicates the final evacuation and, upon repressurization of the chamber to the upper pressure, the end of the conditioning phase of the cycle. The output of the zero line of the decoder is connected to one side of AND gate 112. The high pressure level signal from pressure sensor 96 is connected to the other side of AND gate 112 so that, when a high pressure level signal is present and at the same time a signal is present from decoder 110, AND gate 112 is effective to pass a signal stopping the conditioning cycling and signalling the commencing of the sterilization phase of the cycle.

Each time that button 106 is pressed, pulse selector 104 generates a pulse on the count line input to counter 102 to up-count the counter. In the embodiment shown, button 106 has been pressed four (4) times to effectively load the number "4" into the counter 102. This number can be preset.

With the up-down counter pre-loaded with the number of pulses corresponding to the number of pressure pulses in the conditioning phase of the sterilization cycle, a start signal is generated by any convenient means such as manually closing a conventional on-off switch connected in the main power circuit of the control. The start signal actuates vacuum pump 52 and opens control valve 58 to thereby immediately commence evacuation of the chamber 16. Either simultaneous with the commencement of evacuation, or at a predetermined time thereafter, valve 40 is opened to admit steam to flow, at a rate controlled by the setting of flow-restrictor 42, into the chamber 16 while continuing to evacuate the chamber. Throughout the remainder of the conditioning phase of the cycle, operation is under control of the absolute pressure responsive pressure-sensing assembly 96 which continuously monitors the absolute pressure within the chamber 16, as previously described. This pressure is preferably continuously recorded by a conventional pressure recorder, the output of which is plotted against time and illustrated in FIG. 4, which shows the pressure within the chamber 16 at the start of the cycle to be 760 mm Hg., or one atmosphere.

The controller 100 includes a timing system which monitors the time required for the conditioning phase of the cycle and aborts the cycle when an excessive amount of time is required to reach the sterilizing phase. This timing system can abort the cycle after termination of the conditioning phase, as shown schematically in FIG. 3, or alternatively can abort the cycle after a predetermined time, regardless of whether or not the conditioning phase has been completed. In the system shown in FIG. 3, the start signal which commences the cycle also starts a pulse generator 114 which supplies the pulses to a pre-loaded down-counter 116. The down-counter 116 is a conventional, commercially-available item which is down-counted by the pulses from generator 114.

The outputs of the down-counter 116 are connected to a decoder 118, each output line of which is representative of a number of pulses counted by the down-counter. When the preset number of pulses has been down-counted to zero, then the zero output line of the decoder 118 has a signal thereon, signalling that the down-counter has timed out, i.e., that a predetermined time has lapsed since the start signal started the pulse generator and commenced the conditioning phase of the cycle. The output signal from decoder 118 sets a latch 120 which, in turn, latches a signal onto one input of AND gate 122.

The output signal of AND gate 112 is fed into the other side of AND gate 122 so that, when a signal is present on the input line from latch 120 and from AND gate 112, AND gate 122 produces an output signal which aborts the cycle and can energize a suitable signal such as a buzzer, warning light, or the like.

The output from AND gate 112 also applies a stop signal to pulse generator 114 and resets down-counter 116. Thus, if a signal is present from AND gate 112 indicating that the conditioning phase has been completed prior to the timing out of pre-loaded down-counter 116, no signal will be received from decoder 118 to AND gate 122. Under these conditions, the signal from up-down counter 102, through AND gate 112, will be effective to continue the sterilization cycle by the admission of sterilizing gas into chamber 16.

The start signal, which starts the pulse generator 114 and commences the complete cycle, is also connected to the re-set of latch 120 so that any previously set signal is erased at the beginning of each cycle.

Measuring the time lapse during the conditioning phase of the cycle or portions thereof, and aborting the cycle in the event of excessive time, guards against the application of biocidal sterilants such as ethylene oxide gas to a possibly defective sterilizer. Thus, a leak in the sterilizer seal can result in an excessive amount of time required to reach vacuum, thereby causing the timing mechanism to time out prior to completion of the conditioning phase. By sensing this excessive time and aborting the cycle prior to admitting the sterilizing gas, any potential hazard from such a leak is minimized.

The upper predetermined subatmospheric pressure is indicated in FIG. 4 as being 90 mm Hg. abs. As is known from standard steam tables, this pressure will produce a temperature within the chamber of about 122° F. When sterilization is to be completed in chamber 16 immediately following completion of the conditioning cycle, this upper pressure is selected so as to produce a maximum temperature within the chamber which is slightly, preferably about 5°-8° F., below sterilization temperature of about 130° F. This permits a slight increase in chamber temperature without exceeding the desired 130° F. temperature when the biocidal sterilization gas is admitted into the chamber at a pressure above the upper predetermined pressure.

Figure 5:
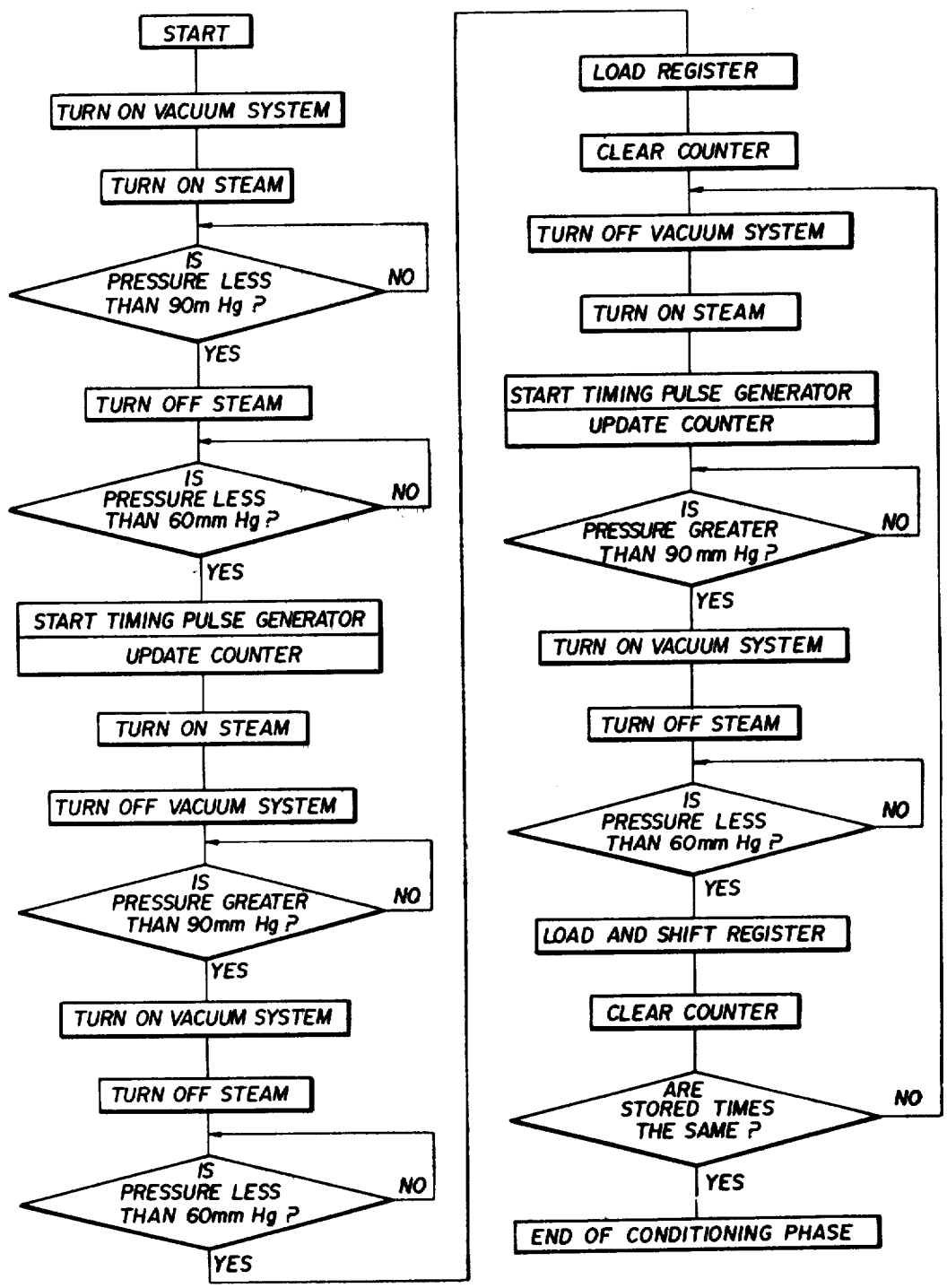
FIG. 5 is a process flow chart for carrying out a conditioning cycle in accordance with an embodiment of the invention in which conditioning is terminated when two successive pressure pulses exhibit substantially the same characteristics.

Referring to FIG. 5, a flow chart illustrating the successive steps of the conditioning phase utilizing the repressurization timing and comparing system is illustrated. From this flow chart, it is seen that the sequence of steps is identical to that described above with the exception that, after each lower predetermined pressure is reached, the time required for the pressure to return to the upper predetermined pressure level is measured and compared with the corresponding time of the preceding pulse. When two such successive times are substantially equal, that load is conditioned and the conditioning phase can be terminated regardless of the number of pulses.

Figure 6:
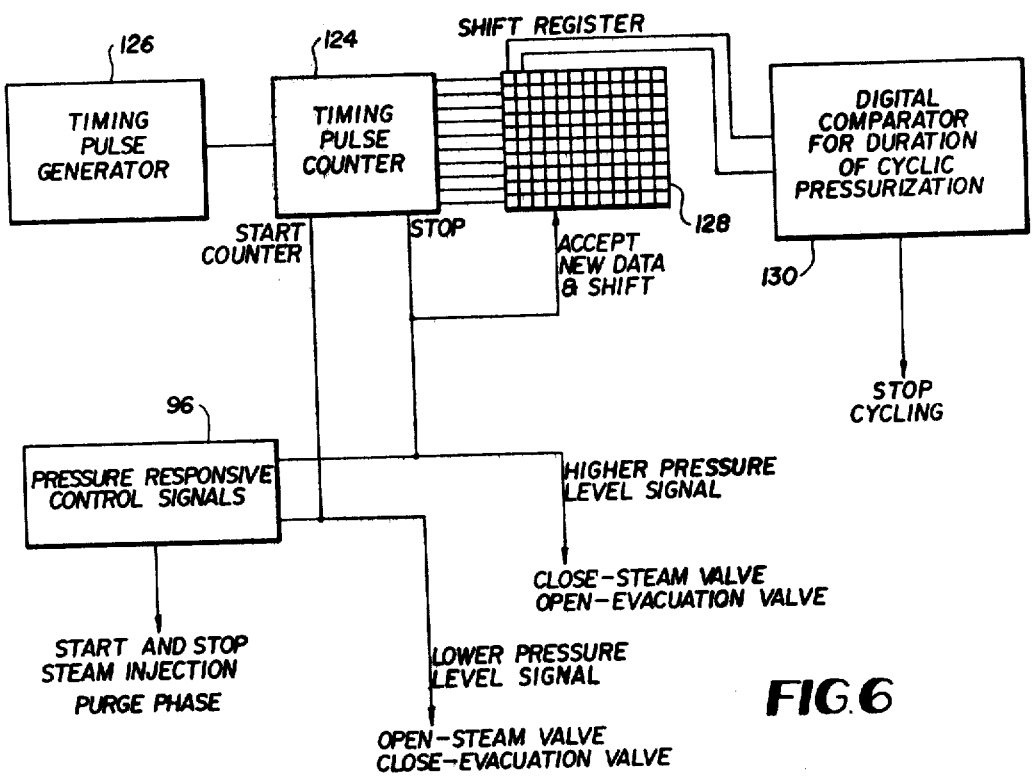
FIG. 6 is a schematic representation of control logic apparatus for carrying out conditioning in accordance with the process of FIG. 5.
Figure 7:
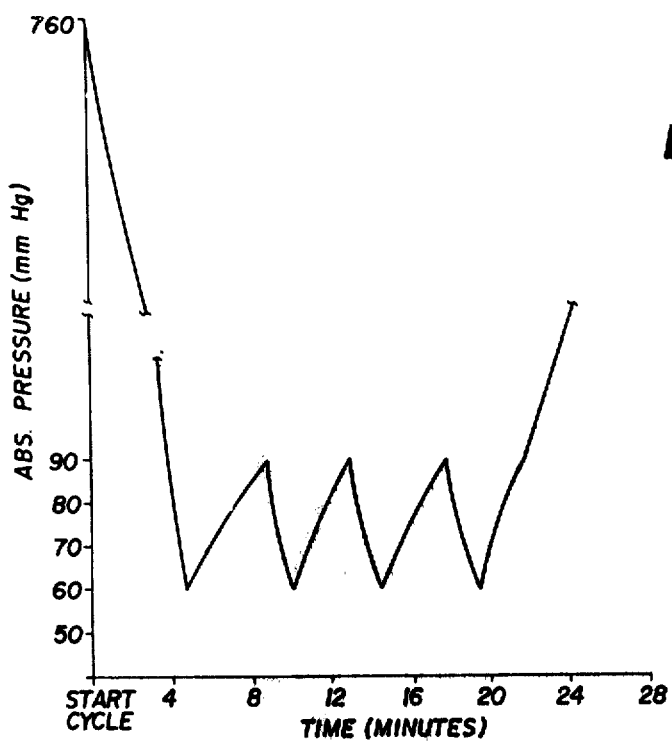
FIG. 7 is a graphic representation of chamber pressure versus time through the conditioning phase of FIG. 5, of a minimal fabric loaded chamber in accordance with the invention.

FIGS. 5-7 illustrate the operation of the embodiment of the invention wherein the control system terminates the conditioning phase when two successive pulse repressurizations require substantially the same time. In this embodiment, the pressure responsive control signals are also directed to a conventional timing pulse counter 124 which, in turn, is connected to a conventional timing pulse generator 126. The initial low pressure signal starts the timing pulse counter which continues to operate and feed timing pulses to a shift register until a high pressure level signal is received which stops the timing pulse counter and conditions the shift register 128 of the timing pulse counter to accept the data in the first register position. The time between the low and high pressure signals is thus stored in the first register position. When a second low pressure signal is received, the timing pulse counter is again started and runs continuously until a second high pressure control signal is received. The second high pressure control signal also conditions the shift register to accept the new timing data from the timing pulse counter and to shift the data from the preceding pressurization pulse phase to the second position. At this point, a digital comparator 130 compares the duration of the two timed pulses and, if the times are the same, within predetermined limits, a signal is emitted stopping the cycling. If, however, the times are not within acceptable limits, the cycling is repeated until the comparator, comparing the times of the last two successive repressurization cycle phases, is within acceptable limits, or, alternatively, the up-down counter mechanism described above can override the comparator control and stop the cycling after four complete pulses regardless of the times for the third and fourth repressurization pulse phases. As with the embodiment shown in FIG. 3, this embodiment can include timing means for aborting the cycle in the event that excessive time is required for the conditioning phase.

Figure 8:
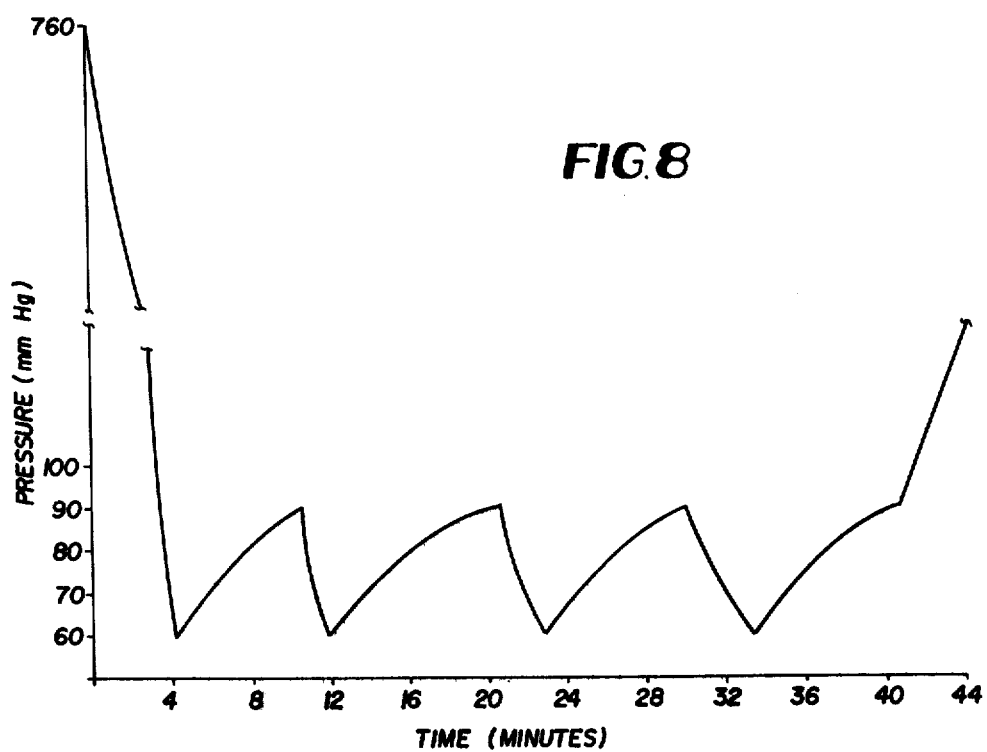
FIG. 8 is a graphical representation of chamber pressure versus time during conditioning of a full fabric load in accordance with the invention.

FIG. 8 shows a cycle wherein the conditioning was terminated after three repressurization pulse phases. As illustrated, the time of repressurization of the second and third phases are substantially equal. Termination of the cycle, as well as the length of time required for the individual pulses, was determined by the characteristics of the load rather than by any predetermined time or temperature consideration.

The conditioning and sterilizing apparatus of the invention can be controlled by a micro-processor programmed to accomplish the various functions and sequence of steps described above. Accordingly, it is contemplated that such a processor may be employed in place of the control system described with reference to FIGS. 3 and 6 to control operation of the apparatus to perform the process described.

A number of tests have been conducted in order to prove the effectiveness and efficiency of the method and apparatus of this invention. Microbiological data was collected using a 24"×36"×48" sterilizing chamber, with the controls functioning to subject the chamber to the conditioning and sterilization cycle described above. Ethylene oxide gas was used as the biocidal agent during the sterilizing phase of the cycle.

The testing employed standard biological indicators (BI's) containing $10^6$ spores of *Bacillus subtilis* (globigii) on filter paper strips. Standard culture procedures were used to evaluate the BI's following the exposure in the test process. The BI's were placed inside two different types of test packs to determine sterilizing efficacy. The test packs were assembled as described in the proposed Canadian Standard Association document, "CSA Standard Z314.2 Guide for Effective Sterlization in Hospitals by the Ethylene Oxide Process". The test packs employed included challenge test packs as defined by Sec. 7.2.2 and routine test packs as defined by Sec. 7.3 of that document.

Tests were conducted using progressively longer sterilization exposure times until an exposure time was established after which no BI in the test pack tested positive. When this result was obtained, a series of at least five (5) tests were conducted at that exposure time to establish repeatability of the test results.

The average ethylene oxide gas concentration for the tests was 713 mg/l. All gas samples were less than ±10% from the average. All tests were conducted with the chamber temperature equilibrated at 130° F.

Comparative tests were also conducted on routine test packs and challenge packs employing a commercially available ethylene oxide sterilizer operated according to the recommended procedure for that sterilizer. These tests were conducted using a steam-flow through conditioning cycle in order to provide a basis of comparing the present invention with what has been generally recognized as the shortest and most rapid gas sterilizing cycle presently available commercially.

The average ethylene oxide gas concentration for the comparative tests was 719 mg/l. All gas samples were less than ±10% from the average. All tests were conducted with the chamber temperature equilibrated at 130° F.

A comparison of the test data obtained from use of the present invention with that obtained by using the commercially available and accepted sterilizer of the same size reveals that the effective conditioning obtained by the present invention results in the complete and reliable sterilization of the test packs with less exposure time than required using the available sterilizer.

While specific embodiments of the invention have been disclosed and described, it is to be understood that adaptation of structure, steps, and materials will be available to those skilled in the art in the light of the present disclosure. For example, while steam is generally considered the most practical conditioning vapor, solvents such as alcohols, ketones, and ethers can be used in conjunction with steam by taking into account the effect on the temperature-pressure interrelationship. Also, the temperature of operation can be selected based on the biocidal gas; in general, ethylene oxide cycles would be carried out at a temperature of about 100° F. to about 150° F. Therefore, it is to be understood that various changes and modifications may be made to the details of the foregoing without departing from the spirit and scope of the invention.

We claim:

1. Apparatus for conditioning goods in a sealed chamber and for subsequently sterilizing said goods with a chemical biocidal agent, the conditioning including moistening and heating to a desired temperature by subjecting the chamber and goods to a plurality of cyclic pressure pulses between predetermined subatmospheric pressure levels, comprising, in combination, a conditioning and sterilizing chamber capable of being evacuated to desired vacuum levels and operable within a maximum prescribed leakage rate, first inlet conduit means connecting the chamber to a second inlet conduit means connecting the chamber to a source of a chemically biocidal agent source of conditioning vapor, first inlet valve means connected in the first inlet conduit means and second inlet valve means connected in the second inlet conduit means and including power means for operating said second valve means to control the flow of chemical biocidal agent into the chamber including power means for operating said first valve means to control the flow of conditioning vapor into the chamber, evacuation means for evacuating the chamber, exhaust conduit means connecting the chamber to the evacuation means, exhaust valve means connected in the exhaust conduit means and including power means for operating the exhaust valve to control the flow through the exhaust conduit to thereby control evacuation of the chamber by the evacuation means, pressure sensing means including means for sensing lower and upper predetermined subatmospheric pressure levels in the chamber and for transmitting a signal in response to the sensing of such pressure levels, and control means including means responsive to signals from the pressure sensing means including, means for generating operating signals for subjecting the chamber to a plurality of cyclic subatmospheric pressure pulses independent of preselected time intervals, and means for operating the power means of the exhaust and first inlet valve means in response to the generated operating signals to non-simultaneously and alternately open the exhaust valve means and close the first inlet valve means to exhaust the chamber to a lower predetermined subatmospheric pressure and to close the exhaust valve means and open the first inlet valve means to increase the pressure within the chamber to an upper predetermined subatmospheric pressure to control such cyclic subatmospheric pressure pulsing, said control means further including means operable at the termination of said conditioning for opening said second inlet valve means for initiating chemical biocidal sterilization.

2. The invention as defined in claim 1 wherein the means for generating operating signals generates signals for operating the power means of the first inlet and the exhaust valve means to initially open both the exhaust valve means and the first inlet valve means to simultaneously evacuate the chamber and admit conditioning vapor into the chamber, prior to commencing the cyclic pulsing to purge air from the chamber to initiate a conditioning cycle.

3. The invention as defined in claim 1 wherein the means for operating the power means of the exhaust and first inlet valve means includes means to open both the first inlet and exhaust valve means at the beginning of a conditioning cycle prior to commencing the cyclic pulsing, means operating the power means of the first inlet valve means to close the first inlet valve means in response to a signal from the pressure sensing means upon sensing of an upper predetermined subatmospheric pressure to prevent further flow of conditioning vapor into the chamber while permitting continued evacuation of the chamber, and means operating the power means of the first inlet and the exhaust valve means to open the first inlet valve means and close the exhaust valve means in response to a signal from the pressure sensing means upon sensing a lower predetermined subatmospheric pressure to thereby permit conditioning vapor to flow into the chamber while stopping the evacuation thereof to thereby increase the pressure within the chamber to the upper predetermined subatmospheric pressure to complete one subatmospheric pressure pulse cycle, the means operating the power means of the first inlet and exhaust valve means being operable thereafter to reverse the open-closed condition of both the first inlet and the exhaust valve means upon sensing of each successive predetermined subatmospheric pressure level to thereby subject the chamber to a plurality of such cyclic subatmospheric pressure pulses.

4. The invention as defined in claim 1 wherein the control means includes counter means operable to count the number of subatmospheric pressure pulses within the chamber, and means for terminating the pressure pulsing after a predetermined number of pulses.

5. The invention as defined in claim 1 wherein the means for generating operating signals is operable to generate such operating signals for maintaining the pressure within the chamber between the same fixed upper and fixed lower preselected subatmospheric pressure levels during each of the plurality of cyclic subatmospheric pressure pulses.

6. The invention as defined in claim 5 wherein the control means includes timing means for measuring the time interval between such lower and such upper preselected subatmospheric pressure levels during consecutive cyclic pressure pulses, means for comparing such consecutive pulse measured times, and means for terminating the conditioning cycle when measured times of such two consecutive pulses are substantially equal.

7. The invention as defined in claim 6 wherein the control means includes counter means operable to count the number of subatmospheric pressure pulses within the chamber, and override means for terminating the pressure pulsing after a predetermined number of pulses, regardless of measured times of consecutive pulses.

8. The invention as defined in claim 7 wherein the counter means includes means enabling the preselecting of the number of pressure pulses prior to initiation of a conditioning cycle.

9. The invention as defined in claim 8 wherein the means for sensing the predetermined subatmospheric pressures senses pressures and generates signals at preselected atmospheric pressure levels between about 50 mm Hg. abs. and 100 mm Hg. abs.

* * * * *